(12) United States Patent
Simonson

(10) Patent No.: US 8,235,999 B2
(45) Date of Patent: Aug. 7, 2012

(54) CONFIGURED AND SIZED CANNULA

(75) Inventor: Robert E. Simonson, Boca Raton, FL (US)

(73) Assignee: DePuy Spine, Inc., Raynham, MA (US)

( * ) Notice: Subject to any disclaimer, the term of this patent is extended or adjusted under 35 U.S.C. 154(b) by 85 days.

(21) Appl. No.: 12/776,857

(22) Filed: May 10, 2010

(65) Prior Publication Data

US 2010/0222824 A1    Sep. 2, 2010

Related U.S. Application Data

(60) Continuation of application No. 11/030,218, filed on Jan. 6, 2005, which is a division of application No. 10/021,809, filed on Oct. 30, 2001, now Pat. No. 7,008,431.

(51) Int. Cl.
*A61B 17/88* (2006.01)

(52) U.S. Cl. ...................... 606/86 A; 606/279

(58) Field of Classification Search ............... 606/86 R, 606/86 A, 96, 104, 105, 190, 191, 279, 250–264, 606/278; 600/205–210, 219, 462; 604/164.1, 604/239

See application file for complete search history.

(56) References Cited

U.S. PATENT DOCUMENTS

| | | |
|---|---|---|
| 569,839 A | 10/1896 | Roeloffs |
| 1,633,703 A | 6/1927 | Kaji |
| 2,922,420 A | 1/1960 | Cheng |
| 3,470,872 A | 10/1969 | Grieshaber |
| 3,875,595 A | 4/1975 | Froning |
| 4,232,660 A | 11/1980 | Coles |
| 4,440,168 A | 4/1984 | Warren |
| 4,449,532 A | 5/1984 | Storz |
| 4,481,947 A | 11/1984 | Chester |
| 4,545,374 A | 10/1985 | Jacobson |
| 4,573,448 A | 3/1986 | Kambin |
| 4,617,922 A | 10/1986 | Griggs |
| 4,620,460 A | 11/1986 | Gonzales, Jr. |
| 4,686,972 A | 8/1987 | Kurland |

(Continued)

FOREIGN PATENT DOCUMENTS

WO     0018306 A1     4/2000

(Continued)

OTHER PUBLICATIONS

U.S. Appl. No. 10/165,991, filed Jun. 10, 2002, Robert E. Simonson.

(Continued)

*Primary Examiner* — Eduardo C Robert
*Assistant Examiner* — Tara Carter
(74) *Attorney, Agent, or Firm* — Nutter McClennen & Fish LLP

(57) ABSTRACT

A dilator retractor and the dilators that are used for minimally invasive spinal surgery or other surgery are configured to accommodate the anatomical structure of the patient as by configuring the cross sectional area in an elliptical shape, or by forming a funnel configuration with the wider end at the proximate end. In some embodiments the distal end is contoured to also accommodate the anatomical structure of the patient so that a cylindrically shaped, funnel shaped, ovoid shaped dilator retractor can be sloped or tunneled to accommodate the bone structure of the patient or provide access for implants. The dilator retractor is made with different lengths to accommodate the depth of the cavity formed by the dilators.

8 Claims, 6 Drawing Sheets

U.S. PATENT DOCUMENTS

| | | | |
|---|---|---|---|
| 4,736,738 A | 4/1988 | Lipovsek et al. |
| 4,747,394 A | 5/1988 | Watanabe |
| 4,798,111 A | 1/1989 | Cheeseman |
| 4,803,976 A | 2/1989 | Frigg et al. |
| 4,808,157 A | 2/1989 | Coombs |
| 4,817,587 A | 4/1989 | Janese |
| 4,862,891 A | 9/1989 | Smith |
| 4,863,423 A | 9/1989 | Wallace |
| 4,872,451 A | 10/1989 | Moore et al. |
| 4,882,958 A | 11/1989 | McNeeley |
| 4,952,214 A | 8/1990 | Comparetto |
| 4,969,888 A | 11/1990 | Scholten et al. |
| 5,035,232 A | 7/1991 | Lutze et al. |
| 5,048,379 A | 9/1991 | Gramera et al. |
| 5,052,373 A | 10/1991 | Michelson |
| 5,084,043 A | 1/1992 | Hertzmann et al. |
| 5,098,435 A | 3/1992 | Stednitz et al. |
| 5,106,376 A | 4/1992 | Mononen et al. |
| 5,133,720 A | 7/1992 | Greenberg |
| 5,135,525 A | 8/1992 | Biscoping et al. |
| 5,148,724 A | 9/1992 | Rexford |
| 5,158,543 A | 10/1992 | Lazarus |
| 5,171,279 A | 12/1992 | Mathews |
| 5,195,541 A | 3/1993 | Obenchain |
| 5,242,443 A | 9/1993 | Kambin |
| 5,275,611 A | 1/1994 | Behl |
| 5,279,567 A | 1/1994 | Ciaglia et al. |
| 5,292,309 A | 3/1994 | Van Tassel et al. |
| 5,303,694 A | 4/1994 | Mikhail |
| 5,312,360 A | 5/1994 | Behl |
| 5,342,384 A | 8/1994 | Sugarbaker |
| 5,356,413 A | 10/1994 | Martins et al. |
| 5,363,841 A | 11/1994 | Coker |
| 5,403,264 A | 4/1995 | Wohlers et al. |
| 5,431,639 A | 7/1995 | Shaw |
| 5,431,651 A | 7/1995 | Goble |
| D361,381 S | 8/1995 | Koros et al. |
| 5,439,464 A | 8/1995 | Shapiro |
| 5,472,426 A | 12/1995 | Bonati et al. |
| 5,489,274 A | 2/1996 | Chu et al. |
| 5,512,038 A | 4/1996 | O'Neal et al. |
| 5,562,677 A | 10/1996 | Hildwein et al. |
| 5,569,248 A | 10/1996 | Mathews |
| 5,601,550 A | 2/1997 | Esser |
| 5,611,778 A | 3/1997 | Brinon |
| 5,687,739 A | 11/1997 | McPherson et al. |
| 5,716,415 A | 2/1998 | Steffee |
| 5,728,097 A | 3/1998 | Mathews |
| 5,743,853 A | 4/1998 | Lauderdale |
| 5,746,720 A | 5/1998 | Stouder, Jr. |
| 5,766,221 A | 6/1998 | Benderev et al. |
| 5,792,044 A | 8/1998 | Foley et al. |
| D399,955 S | 10/1998 | Koros et al. |
| 5,816,257 A | 10/1998 | Chin |
| RE36,020 E | 12/1998 | Moore et al. |
| 5,851,207 A | 12/1998 | Cesarone |
| 5,882,344 A | 3/1999 | Stouder, Jr. |
| 5,885,299 A | 3/1999 | Winslow et al. |
| 5,885,300 A | 3/1999 | Tokuhashi et al. |
| 5,891,147 A | 4/1999 | Moskovitz et al. |
| 5,895,352 A | 4/1999 | Kleiner |
| 5,895,390 A | 4/1999 | Moran et al. |
| 5,897,593 A | 4/1999 | Kohrs et al. |
| 5,899,901 A | 5/1999 | Middleton |
| 5,902,231 A | 5/1999 | Foley et al. |
| 5,913,818 A | 6/1999 | Co et al. |
| 5,928,139 A | 7/1999 | Koros et al. |
| 5,944,658 A | 8/1999 | Koros et al. |
| 5,954,635 A | 9/1999 | Foley et al. |
| 5,954,671 A | 9/1999 | O'Neill |
| 5,967,970 A | 10/1999 | Cowan et al. |
| 5,971,920 A | 10/1999 | Nagel |
| 5,976,146 A | 11/1999 | Ogawa et al. |
| 5,996,447 A | 12/1999 | Bayouth |
| 6,004,322 A | 12/1999 | Bernstein |
| 6,007,487 A | 12/1999 | Foley et al. |
| 6,010,520 A | 1/2000 | Pattison |
| 6,033,406 A | 3/2000 | Mathews |
| 6,063,088 A | 5/2000 | Winslow |
| 6,080,155 A | 6/2000 | Michelson |
| 6,081,741 A | 6/2000 | Hollis |
| 6,083,225 A | 7/2000 | Winslow et al. |
| 6,113,602 A | 9/2000 | Sand |
| 6,120,434 A | 9/2000 | Kimura et al. |
| 6,120,506 A | 9/2000 | Kohrs et al. |
| D433,296 S | 11/2000 | Yamakawa |
| 6,152,871 A | 11/2000 | Foley et al. |
| 6,156,006 A | 12/2000 | Brosens |
| 6,159,179 A | 12/2000 | Simonson |
| 6,162,170 A | 12/2000 | Foley et al. |
| 6,162,236 A | 12/2000 | Osada |
| D436,513 S | 1/2001 | Yamakawa |
| 6,176,823 B1 | 1/2001 | Foley et al. |
| D438,074 S | 2/2001 | Marr et al. |
| 6,197,002 B1 | 3/2001 | Peterson |
| 6,206,822 B1 | 3/2001 | Foley et al. |
| 6,206,826 B1 | 3/2001 | Mathews et al. |
| 6,206,885 B1 | 3/2001 | Ghahremani et al. |
| 6,214,004 B1 | 4/2001 | Coker |
| 6,217,509 B1 | 4/2001 | Foley et al. |
| 6,224,597 B1 | 5/2001 | Coker |
| 6,224,608 B1 | 5/2001 | Ciccolella et al. |
| 6,241,734 B1 | 6/2001 | Scribner et al. |
| 6,245,072 B1 | 6/2001 | Zdeblick et al. |
| 6,258,097 B1 | 7/2001 | Cook et al. |
| 6,267,763 B1 | 7/2001 | Castro |
| 6,270,498 B1 | 8/2001 | Michelson |
| 6,273,896 B1 | 8/2001 | Franck et al. |
| 6,283,966 B1 | 9/2001 | Houfburg |
| 6,287,313 B1 | 9/2001 | Sasso |
| 6,296,609 B1 | 10/2001 | Brau |
| 6,312,432 B1 | 11/2001 | Leppelmeier |
| 6,342,057 B1 | 1/2002 | Brace et al. |
| 6,348,058 B1 | 2/2002 | Melkent et al. |
| 6,354,176 B1 | 3/2002 | Nordlin |
| 6,371,959 B1 | 4/2002 | Trice |
| 6,371,968 B1 | 4/2002 | Kogasaka et al. |
| 6,395,007 B1 | 5/2002 | Bhatnagar et al. |
| 6,418,821 B1 | 7/2002 | Yamakawa |
| 6,428,472 B1 | 8/2002 | Haas |
| 6,461,330 B1 | 10/2002 | Miyagi |
| D466,766 S | 12/2002 | Marty et al. |
| 6,520,907 B1 | 2/2003 | Foley et al. |
| 6,524,238 B2 | 2/2003 | Velikaris et al. |
| 6,530,926 B1 | 3/2003 | Davison |
| 6,530,929 B1 | 3/2003 | Justis et al. |
| 6,540,756 B1 | 4/2003 | Vaughan |
| 6,558,386 B1 | 5/2003 | Cragg |
| 6,607,530 B1 | 8/2003 | Carl et al. |
| 6,692,434 B2 | 2/2004 | Ritland |
| 6,793,656 B1 | 9/2004 | Mathews |
| 6,921,403 B2 | 7/2005 | Cragg et al. |
| 6,929,606 B2 | 8/2005 | Ritland |
| 7,008,424 B2 | 3/2006 | Teitelbaum |
| 7,008,431 B2 | 3/2006 | Simonson |
| 7,435,219 B2 | 10/2008 | Kim |
| 7,476,240 B2 | 1/2009 | Raymond et al. |
| 7,648,506 B2 | 1/2010 | McCord et al. |
| 7,648,507 B2 | 1/2010 | Techiera et al. |
| RE42,525 E | 7/2011 | Simonson |
| 2001/0012942 A1 | 8/2001 | Estes et al. |
| 2001/0027320 A1 | 10/2001 | Sasso |
| 2002/0011135 A1 | 1/2002 | Hall |
| 2002/0016592 A1 | 2/2002 | Branch et al. |
| 2002/0022764 A1 | 2/2002 | Smith et al. |
| 2002/0045904 A1 | 4/2002 | Fuss et al. |
| 2002/0049368 A1 | 4/2002 | Ritland |
| 2002/0058948 A1 | 5/2002 | Arlettaz |
| 2002/0077632 A1 | 6/2002 | Tsou |
| 2002/0082695 A1 | 6/2002 | Neumann |
| 2002/0088695 A1 | 7/2002 | Migimatsu et al. |
| 2002/0123668 A1 | 9/2002 | Ritland |
| 2002/0143235 A1 | 10/2002 | Pagliuca |
| 2002/0161368 A1* | 10/2002 | Foley et al. .......... 606/61 |
| 2003/0083688 A1 | 5/2003 | Simonson |
| 2003/0083689 A1 | 5/2003 | Simonson |
| 2003/0187431 A1 | 10/2003 | Simonson |

| | | |
|---|---|---|
| 2003/0220689 A1 | 11/2003 | Ritland et al. |
| 2003/0236447 A1 | 12/2003 | Ritland |
| 2004/0106997 A1 | 6/2004 | Lieberson |
| 2005/0004593 A1 | 1/2005 | Simonson |
| 2005/0080418 A1 | 4/2005 | Simonson et al. |
| 2005/0085813 A1* | 4/2005 | Spitler et al. ............... 606/61 |
| 2005/0131421 A1 | 6/2005 | Anderson et al. |
| 2005/0136085 A1 | 6/2005 | Bellamy |
| 2005/0137461 A1 | 6/2005 | Marchek et al. |
| 2005/0203490 A1 | 9/2005 | Simonson |
| 2005/0216002 A1* | 9/2005 | Simonson ..................... 606/61 |
| 2007/0134175 A1 | 6/2007 | Bellamy |
| 2010/0222824 A1 | 9/2010 | Simonson |

FOREIGN PATENT DOCUMENTS

WO 02060330 A1 8/2002

OTHER PUBLICATIONS

U.S. Appl. No. 10/899,707, filed Jul. 26, 2004, Robert E. Simonson.
Sofamor Danek, "MED MicroEndoscopic Discectomy System" (1997).
Wolfhard Caspar, Technique of Microsurgery, in Microsurgery of the Lumbar Spine: Principles and Techniques in Spine Surgery 105-122 (Aspen Publications, 1990).
Web page, http://www.brainlab.com, Apr. 2, 2002.
Kambin, Parviz, "Arthroscopic Microdiscectomy: Minimal Intervention in Spinal Surgery", National Library of Medicine, 1991 p. 67-100, Urban & Schwarzenberg.
Schaffer, Johnathan et al., "Percutaneous Posterolateral Lumbar Discectomy and decompression with a 6.9 Millimeter Cannula", The Journal of bone and Joint Surgery, 1991, pp. 822-831.
Savitz, Martin, "Same-Day Microsurgical Arthroscopic Latera-Approach Laser-Assisted (SMALL) Fluoroscopic Discectomy", Journal of Neurosurgery: Jun. 1994, pp. 1039-1045.
Hilton, Donald et al., "Medtronic Sofamor Danek METRX Microdiscectomy Surgical Technique Brochure",2001.
Wiltse, "New Uses and Refinements of the Paraspinal Approach to the Lumbar Spine", Spine, vol. 13, No. 6 1988, pp. 696-706.
Leu, Hans-Jorg and Schreiber, Adam, "Percutaneous Lumbar Restabilization," Arthroscopic Microdiscectomy: Minimal Intervention in Spinal Surgery, pp. 123-125 (1990).
Ozer, "A New Retractor for the Anterior Cervical Approach," Br J Neurosurg, 1994, pp. 469-470, vol. 8(4).
Schetrumpf, Jr., "Combined Retractor and Sucker with Built-in Clearing Device for Spinal Surgery," Injury, 1973, pp. 352-353, vol. 4(4).
Schreiber, et al., "Does Percutaneous Nucleotomy with Discoscopy Replace Conventional Discectomy?", Clinical Orthopaedics and Related Research, No. 238, Jan. 1989.
Sofamor Danek Video Systems Brochure, 10 pages, (1994).
Styf, "The Effects of External Compression by Three Different Retractors on Pressure in the Erector Spine Muscles During and After Posterior Lumbar Spine Surgery in Humans," Spine, 1998, pp. 354-358, vol. 23(3), Lippincott-Raven Publishers.

Barone, "An Improved Retractor for the Anterior Apporach in the Surgical Management of Vertebral Fractures," Am J Orthop, 1998, pp. 703-704, vol. 27(10).
Frank, "Endoscopic Dural Retractor for Spinal Stenosis Surgery," Minim Invasive Neurosurg, 2002, pp. 136-138, vol. 45 (3).
Hsu, Ken et al, "Internal Fixation with Pedicle Screws," Lumbar Spine Surgery, Techniques and Complications, The C. V. Mosby Company pp. 322-338 (1987).
Kambin, Parvis and Schaffer, Johnathan, "Arthroscopic Fusion of the Lumbosacral Spine," Lumbosacral and Spinopelvic Fixation, ch 44, pp. 565-577 (1996).
Kambin, Parvis, "Arthroscopic Lumbar Intervertebral Fusion," The Adult Spine: Principles and Practice, ch. 95, pp. 2037-2046 (1997).
Kambin, Parvis, "Arthroscopic Techniques for Spinal Surgery," Operative Arthroscopy, ch 89, pp. 1215-1225 (1996).
Kambin, Parviz, "Percutaneous Posterolateral Discectomy", Clinical Orthopaedics and Related Research, Section II, pp. 145-154 (1986).
Kambin, Parviz, "Posterolateral Percutaneous Lumbar Interbody Fusion", Arthroscopic Microdiscectomy: Minimal Intervention in Spinal Surgery, pp. 117-121 (1991).
Leu, Hansjoerg Franz et al, "Lumber Percutaneous Endoscopic Interbody Fusion," Clinical Orthopaedics and Related Research, No. 337, pp. 58-63 (1997).
Leu, Hans-Jorg and Schreiber, Adam, "La Nucleotomie Percutanee Avec Discoscopie: Experiences Depuis 1979 Et Possibilities Actuelles," Revue Medicale De La Suisse Romande, vol. 109, pp. 477-482 (1989).
Office Action in U.S. Appl. No. 10/899,707 dated Dec. 8, 2004.
Amendment in U.S. Appl. No. 10/899,707 dated Feb. 5, 2005.
Office Action in U.S. Appl. No. 10/899,707 dated Mar. 31, 2005.
Amendment in U.S. Appl. No. 10/899,707 dated Jul. 5, 2005.
Office Action in U.S. Appl. No. 10/899,707 dated Aug. 16, 2005.
Amendment in U.S. Appl. No. 10/899,707 dated Nov. 16, 2005.
Office Action in U.S. Appl. No. 10/899,707 dated Feb. 7, 2006.
Amendment in U.S. Appl. No. 10/899,707 dated Mar. 13, 2006.
Advisory Action in U.S. Appl. No. 10/899,707 dated Mar. 29, 2006.
Appeal Brief in U.S. Appl. No. 10/899,707 dated May 31, 2006.
Examiner's Answer in U.S. Appl. No. 10/899,707 dated Dec. 13, 2006.
Reply Brief in U.S. Appl. No. 10/899,707 dated Feb. 7, 2007.
Board of Patent Appeals and Interferences Decision in U.S. Appl. No. 10/899,707 dated Dec. 2, 2010.
Amendment in U.S. Appl. No. 10/899,707 dated Feb. 1, 2011.
Office Action in U.S. Appl. No. 10/899,707 dated Mar. 15, 2011.
Amendment in U.S. Appl. No. 10/899,707 dated May 19, 2011.
Office Action in U.S. Appl. No. 10/899,707 dated Jun. 20, 2011.
Amendment in U.S. Appl. No. 10/899,707 dated Dec. 2, 2011.
Office Action in U.S. Appl. No. 10/899,707 dated Dec. 14, 2011.
Office Action in U.S. Appl. No. 12/971,929 dated Nov. 23, 2011.
Office Action in U.S. Appl. No. 12/971,929 dated Apr. 26, 2012.

* cited by examiner

CONFIGURED AND SIZED CANNULA

CROSS-REFERENCE TO RELATED APPLICATIONS

This application is a continuation of U.S. patent application Ser. No. 11/030,218 filed on Jan. 6, 2005 and entitled "Configured And Sized Cannula," which is a divisional of U.S. patent application Ser. No. 10/021,809 filed on Oct. 30, 2001 and entitled "Configured And Sized Cannula," now U.S. Pat. No. 7,008,431, which are expressly incorporated herein by reference in their entireties.

FIELD OF THE INVENTION

This invention relates to medical instruments for use in surgical procedures and more particularly to a wide-channel cannula that is pre-sized, pre-configured and tailored to conform to the patient's anatomy.

BACKGROUND OF THE INVENTION

In one aspect of this invention, the invention considers the anatomical shape of the area of the patient being operated on and tailors the shape of the dilators and the dilator retractor or cannula to accommodate that shape. In another aspect of this invention, the invention constitutes an improvement over the apparatus and method disclosed and claimed in U.S. Pat. No. 6,159,179 granted on Dec. 12, 2000 to the inventor of this patent application and entitled "Cannula and Sizing and Insertion Method" by providing different sizes of the same configuration of dilator retractors.

As is well known by those skilled in this technology, the cannula utilized in the field of minimally invasive surgery is particularly efficacious in performing such spinal medical procedures as laminotomy, medial facetectomy, foraminotomy, nerve root retraction, discectomy and the like, is cylindrically shaped. I have found that a cylindrically shaped cannula is not always ideal for certain surgical procedures and this invention is intended to obviate the problems incidental to a cylindrically shaped cannula and to increase the number of surgical procedures that can be performed by dilation methods by changing the configuration of the retractor tube or cannula. As is apparent to one skilled in this technology, the anatomy of the human spine is not made up of flat surfaces and a purely cylindrical device passed over cylindrical dilators and directed toward the lamina more likely than not settles off of or partly on the bone. When this occurs, a tuft of muscle migrates to or is left between the bone and the bottom of the retractor and must be removed surgically. Obviously, this surgery is a source of pain and discomfort for the patient and creates an additional surgical step for the surgeon. Moreover, this additional surgery causes additional bleeding and as a consequence, creates an obstruction to the vision of the surgeon. In order to cure the obstruction, the surgeon must address this problem through an electro cautery procedure.

Also apparent to one skilled in this technology is that the pathological target within the patient is often not an equal distance vertically and horizontally. Hence, a surgical procedure may require a surgical approach that for ideal conditions, provides access that is more vertical in orientation than lateral. Obviously, a cylindrical device as has been heretofore available and as disclosed in U.S. Pat. No. 6,159,179 supra, which is equidistant from the axis, does not allow for this approach. Thus, in a cylindrical cannula, in order to gain additional vertical access the size of the cannula must be increased the same amount in the lateral direction that it is in the vertical direction. Obviously, the human spine's skeletal structure, i.e. lateral facets and medial spinous process, restricts the amount of lateral space available. In a cylindrical cannula, since a limitation of the lateral space that is available to locate a retractor, the vertical space is likewise limited. As a consequence, the cylindrical cannula limits the number of patients who are candidates for minimally invasive spinal surgery necessitating the more invasive type surgery with all of the problems associated therewith. Hence, for a large segment of the patient population, the only surgery available is the more destructive invasive muscle burning and stripping approach. This invention addresses this problem and provides a solution whereby the minimal invasive surgery is now possible which otherwise was considered impossible to perform, unpractical or unpredictable in terms of surgical success or long-term outcome.

The other aspect of this invention is the improvement to the system claimed in U.S. Pat. No. 6,159,179, supra. In this patent, the depth of the cavity at the location where the invasive procedure is being performed is measured and the surgeon can then select from a kit or inventory of different sized cannulas or retractors the desired size required to perform the surgical procedure.

I have found that a solution to the problem noted in the immediate above paragraphs is that I provide in one embodiment of this invention, dilators and retractors that are configured other than in a cylindrical shape, such as an ovoid, and that I provide different sizes to meet the anatomical needs of a particular patient. By providing dilators and dilator retractors made in accordance with this invention, these instruments will be able to reach down between the facet joint and the spinous process to gently part muscle tissue and come into closer contact to the bony target. This will reduce or eliminate the need for the surgeon to surgically remove otherwise valuable viable muscle tissue. This will also reduce post-operative pain and inter-operative time (fiddle). In addition to the above, this new design will allow surgeons to address new pathologies in patients that previously would not have been able to undergo a minimally invasive technique. To more fully appreciate the importance of this invention a common example is discussed immediately hereinbelow.

This example considers a patient with multilevel central canal stenosis. To address this patient's pathology, the surgeon may need over 35 millimeters (mm) of vertical access. The typical lateral distance, i.e., space between the spinous process and the facet joint, available at the L4 lamina is 16 mm. A 16 mm cylindrical retractor would fit tightly against the lamina but even with "wanding" (moving up and down) it would restrict the surgeons ability to reach much more than the 16 mm in vertical access. The only option that is available to the surgeon, heretofore, is to utilize a cylindrical retractor. As explained above, since the equation for a cylindrical retractor mandates that the lateral and vertical expansions are equal, the cylindrical retractor would quickly reach beyond the practical or acceptable size for many, if not most, multilevel patient candidates.

Another embodiment of this invention is the contouring or configuring of the bottom of the retractor in order to meet the requirements of certain operation procedures and/or permit the retractor to be positioned closer to the target. This invention contemplates angling the tip in both a cylindrical and ovoid shaped retractor and/or locating a tunnel in the bottom thereof which allows for a rod or implant to be passed through the distal tip of the cannula and into a pedicle screw (e.g., as shown in FIG. 5A).

While much has been accomplished in the medical field to limit tissue disruption, use minimal incisions, reduce the hospital stay and increase the speed in which the patient recovers, this invention is intended to raise the surgical procedure to a higher level. This invention in the field of minimally invasive surgery is particularly efficacious in performing such spinal medical procedures as laminotomy, medial facetectomy, foraminotomy, nerve root retraction, discectomy and the like.

As discussed in U.S. Pat. No. 6,159,179, supra, a typical procedure in performing a lumbar discectomy is to advance a guidewire through a small incision which is advanced to the inferior edge of the superior lamina. A small incision is then made that extends either cranially or caudally. A dilator is then inserted over the guidewire. Larger diameter dilators are sequentially inserted over each other to increase the opening into the body cavity. Typically the guide wire is removed after the first dilator is installed and eventually the dilators are all removed after the tubular retractor has been inserted over the largest of the dilators. Once these procedures are accomplished, the retractor is locked into position by a retractor clamp that is clamped to a retractor clamping arm which is fixed to a rigid member such as the operating table. This provides an unencumbered zone where the surgeon can perform the medical procedure that was intended to be performed. According to the present invention, the dilators, of course will now conform to the configuration discussed above.

Instead of sizing the cannula to the largest depth that is anticipated in the surgical procedure, the U.S. Pat. No. 6,159, 179, supra, teaches providing to the surgeon a series of different sizes in a kit so that the surgeon can measure the depth of the cavity of the patient and select the requisite size from the kit. Hence, the surgeon measures the depth by measuring from the exterior of the cavity to the most interior position in the cavity (inferior edge of the superior lamina) and then selects, for example, either a 10 millimeters (mm), 20 mm, 30 mm, etc. as the situation requires. The dilator retractor will also have the same cross sectional shape as the dilator, but it may have a predetermined configuration at the distal end. This invention improves the state of the art of spinal surgery by expanding the current boundaries of minimally invasive surgery. This provides a new option to patients that would otherwise be delegated to the more disruptive open muscle stripping surgical approaches. The ovoid design with or without the angled distal tip, allows a surgeon greater vertical access without having to be encumbered by unnecessary lateral access.

Also, it is contemplated within the scope of this invention, that the dilator retractor will be provided in a kit where a given configuration will be provided in a series of dilator retractors that have different lengths, so that the depth of the cavity of the patient will determine the particular sized dilator retractor that will be utilized for that procedure.

SUMMARY OF THE INVENTION

An object of this invention is to provide a cannula used in minimally invasive technique that is tailored for a patient and pathology.

A feature of this invention is to provide an ovoid shaped retractor and a complementary shaped dilators. Other configurations that are not cylindrical are contemplated within the scope of this invention.

Another feature of this invention is to contour the tip of the distal end of the retractor to match the bone structure in the patient.

Another feature of this invention is to provide an access channel at the distal end of the retractor to allow passage of medical hardware.

Another feature of this invention is to provide retractors that are made from a series of predetermined sizes having tailored contouring that the surgeon can select to match the depth of the cavity in the patient made by the dilator.

The foregoing and other features of the present invention will become more apparent from the following description and accompanying drawings.

These figures merely serve to further clarify and illustrate the present invention and are not intended to limit the scope thereof.

DETAILED DESCRIPTION OF THE INVENTION

While the preferred embodiment of this invention is described herein, it will be appreciated, as one skilled in this art will recognize, that the invention although directed toward non-cylindrically shaped dilator retractors, under certain circumstances, the invention contemplates cylindrically shaped dilator retractors where the bottom or distal end is configured to accommodate the shape of the bone structure of the patient or to accommodate different procedures that are available to the surgeon. As for example, the distal end of a cylindrically shaped dilator retractor may be tunneled so as to allow the insertion of an implant. The terms "cannula" and "dilator retractor" have the same meaning and are used herein interchangeably. The term cavity as used herein means the cavity that is created by the dilators and when the dilator retractor is inserted in this cavity it becomes a working channel for the surgeons use in performing the minimal invasive surgery. While the invention is particularly efficacious for use in performing minimal invasive surgery, as would be obvious to any skilled artisan, this invention would also be useful for other types of surgery.

While in the preferred embodiment the description of this invention details the use of a non cannulated dilator of the type described and claimed in the Cross Reference of this patent application and which is incorporated herein by reference, as one skilled in the art will appreciate, this invention also contemplates the use of a guide wire for certain surgical procedures.

To better understand this invention reference is made to the prior art configuration of a dilator retractor as viewed in the target area of a patient. In this example, the patient is inflicted with a herniated disc in the spinal column and the surgeon targets the posterior portion of the vertebra to perform the surgical procedure. The dilator retractor or cannula 10 is inserted in the body and up to where the distal end rests on the bone structure. Obviously, there is a space from left to right between the bone and the end of the dilator retractor and as mentioned above, tufts of muscle remains in or migrates to this area. The surgeon needs to remove this material before performing the procedure for repairing the herniated disc to the discomfort of the patient.

Figure 1:
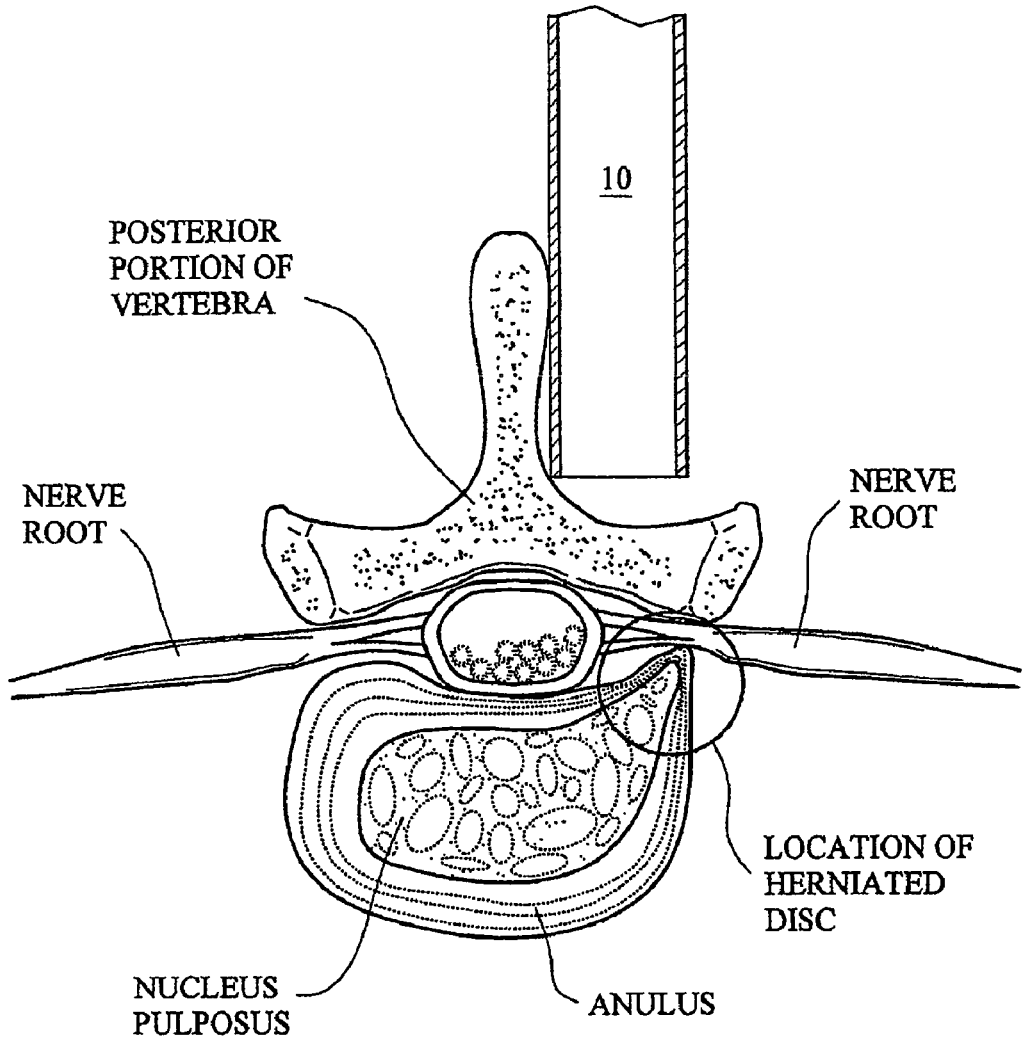
FIG. 1 is a schematic illustration of the spine of a patient with the cannula shown in cross section inserted adjacent to the posterior portion of the vertebra and having superimposed the cannula resting on the bone of a prior art configuration.
Figure 2:
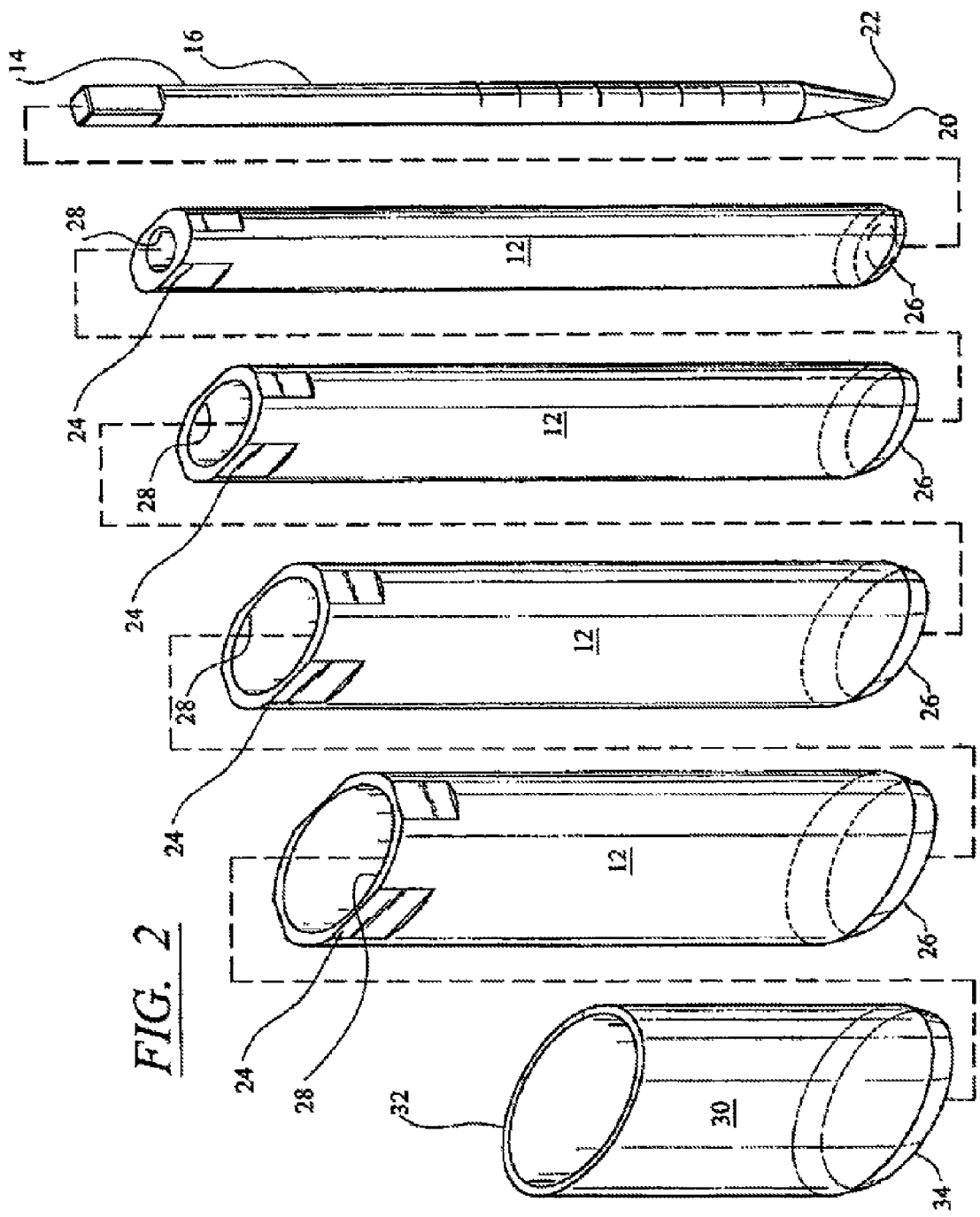
FIG. 2 is an exploded view in perspective of the non cannulated dilator, a series of graduated increased diameter dilators and the cannula or dilator retractor of this invention.
Figure 3:
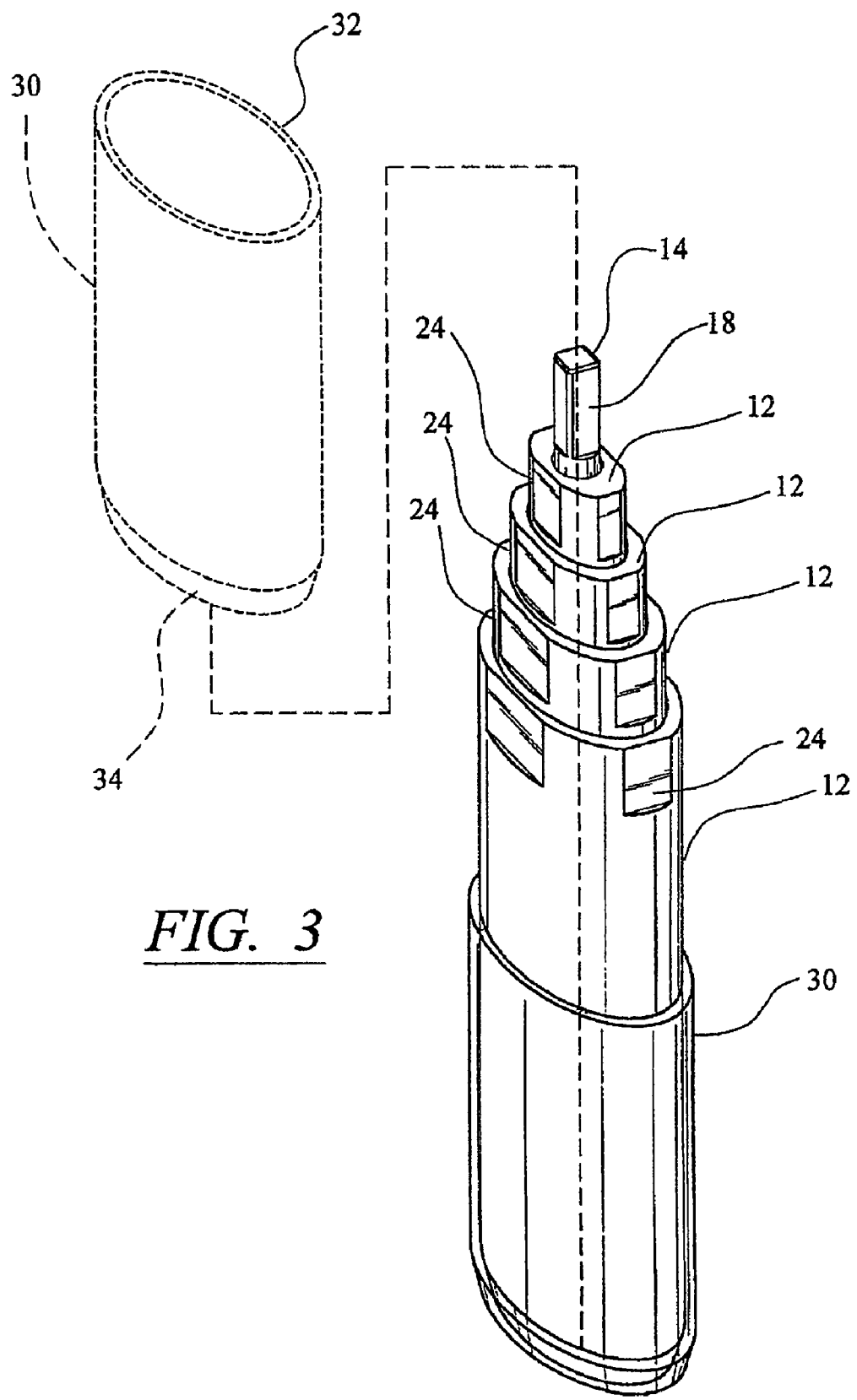
FIG. 3 is a view in perspective illustrating the non cannulated dilator, the graduated dilators and the dilator retractor stacked over each other as they would appear in the patient and the dilator retractor shown in phantom when the other elements are removed.

In accordance with one embodiment of this invention and as best seen in FIGS. 2 and 3, a series of dilators 12, including the non-cannula dilator 14 serve to enlarge the cavity of the patient by inserting the first dilator or non-cannula dilator 14 into a incision in the skin of the patient and "working" the non-cannula dilator 14, a tool (not shown) engaging the proximal end by forcing and rocking it through the fibrous and muscle material until it reaches its target. The non-cannula dilator is an elongated cylindrical solid body 16 having a tool engaging portion 18 at the proximate end and a pointed tip portion 20 at the distal end. The tip 22 of the pointed tip portion is blunted and slightly rounded so that it is unlike the tip of a common sewing needle, i.e. not razor sharp. The other dilators 12, being progressively shorter in length are all similarly constructed. Namely, they all are hollow so that each progressively shorter dilator passes over the previously inserted dilator and have a tool engaging end portion 24 at the proximate end and a beveled end portion 26 at the distal end that fares into a sharp edge at the bottom thereof. The dilators function is well known and for the sake of convenience and brevity need not be detailed herein. The inventive aspect of the dilators 12 is that they are configured in an elliptical or ovoid shape in cross section and the circumferential dimension between the tool engaging portion 24 and the beveled end portion 26. The hollow portion of each of the dilators 18 are configured to complement the outer surface of the preceding dilator and in the instance of the non cannula dilator 14, the hollow portion of the next succeeding dilator 12 is circular in cross section rather than being elliptical in cross section as are the next succeeding dilators 12. After the dilators 12 have been inserted into the patient, the dilator retractor 30 is inserted over the last inserted dilator 12 and forced into position, typically with a template or anvil that fits over the proximate end 32 of the dilator retractor 30. The opposite end portion, similar to the dilators 12 is beveled and fares into a sharp edge 34. The hollow portion or straight through bore 26 is contoured identically to the contour of the preceding dilator 12. FIG. 3 demonstrates the positions of the dilators 12 and the non cannula dilator 14 when finally inserted into the patient. As seen in FIG. 3, the dilators 12 and non cannula dilator 14 are removed leaving the dilator retractor 30 in position. Obviously, the dilator retractor 30 affords a wide channel for the surgeon to pass his instruments therethrough allowing the surgeon to perform the surgical procedure while providing sufficient opening to permit the use of a microscope and lighting to view the area of the target.

Figure 4:
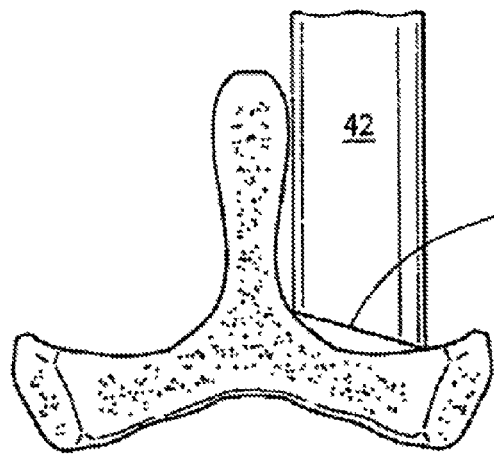
FIG. 4 is a schematic illustrating an embodiment of this invention where the dilator retractor is configured with the distal end being slanted to accommodate the bone structure of the patient.
Figure 5:
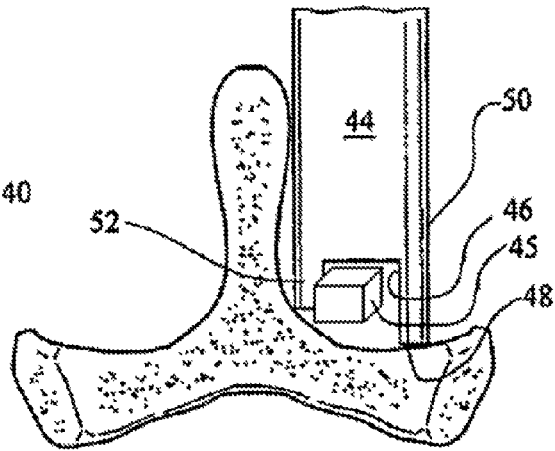
FIG. 5 is a schematic illustration exemplifying another embodiment of this invention where the dilator retractor is configured with a tunnel at the distal end.
Figure 5A:
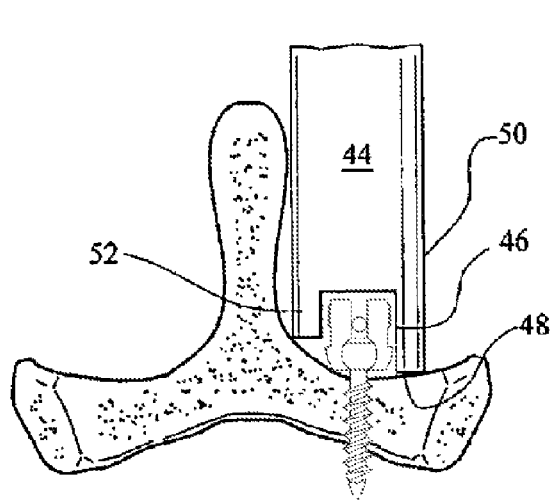
FIG. 5A is a schematic illustration of the embodiment of FIG. 5 shown in proximity to a pedicle screw implanted in a vertebra.
Figure 6:
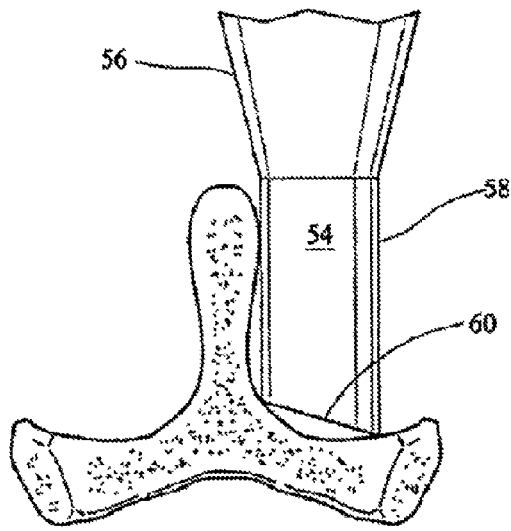
FIG. 6 is a schematic illustration exemplifying another embodiment of this invention where the dilator retractor is configured in a funnel shape.

As mentioned in the Background section of this patent application, in accordance with this invention the distal ends of the dilator retractors are "tailored" to meet certain criteria resulting from the anatomical structure of the target area of the patient. FIGS. 4, 5, and 6 exemplify examples of what is meant by the term "tailoring" and while these dilator retractors represent the preferred embodiment, it will be understood by those skilled in this art that these are merely examples and do not limit the scope of this invention. In FIG. 4, for example, the distal end 40 of dilator retractor 42 is sloped to follow to some degree the slope of the posterior portion of the vertebra. The direction of the slope and the degree of the slope will be predicated on statistical dimensions of these bone structure for a variety of different sized individuals. The cross sectional configuration of the dilator retractor 42 can take any of a number of different shapes, such as elliptical, circular, etc.

FIG. 5 is similar in concept to FIG. 4 except that the dilator retractor 44 includes a cut-out portion 46 at the distal end 48 and side 50 is longer than side 52 or like the dilator retractor 42 depicted in FIG. 4, the bottom portion can be sloped. Since the cut-out portion 46 is made through the side walls and bore of the dilator and dilator retractor, it is essentially a cut out of the side walls at diametrical locations at the distal end and hence, defines a lateral passageway or tunnel to allow passage of an implant 45.

The dilator retractor 54 of FIG. 6 is similar to the dilator retractor depicted in FIG. 4 except that the configuration is funnel shaped. Namely, the upper portion 56 is conically shaped with the wider portion at the proximal end and fares into the cylindrical portion 58. The distal end 60 is sloped similar to the slope in the dilator retractor 42 depicted in FIG. 4. Obviously, the wider proximal end affords a wider channel that is available for use by the surgeon.

It is apparent from the foregoing and particularly with the embodiments depicted in FIGS. 4 and 5, the configuration of the dilator retractors can take many shapes, namely cylindrical, elliptical or even polygon shape. Of course, in the preferred embodiment, the thickness of the wall over the major portion of the dilator retractors are uniform.

Figure 7:
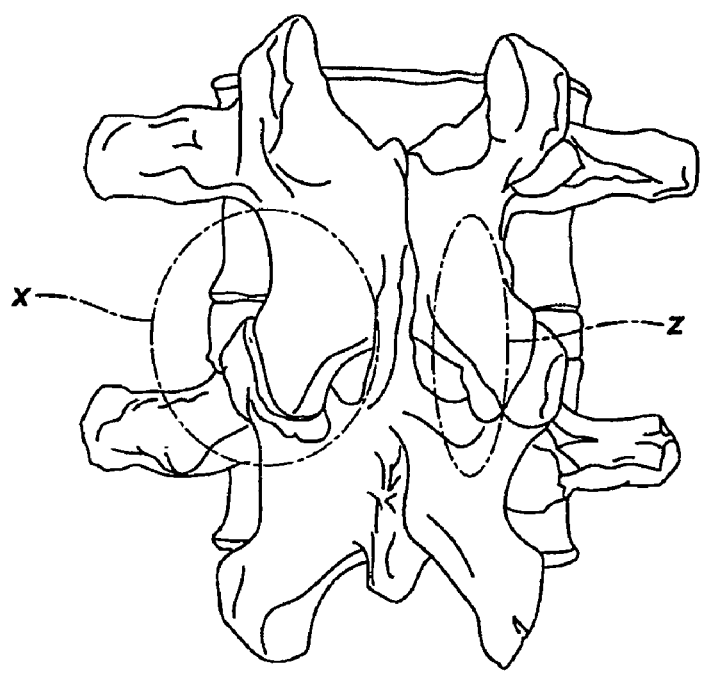
FIG. 7 is a photocopy of a drawing of the posterior view of the $3^{rd}$ and $4^{th}$ lumbar vertebrae with a schematic comparison of a circular in cross section configured prior art dilator retractor and the dilator retractor of this invention.

FIG. 7 is included to illustrate the comparison of the heretofore known dilator retractors or cannulas and the dilator retractors or cannulas made in accordance with certain embodiments of this invention. FIG. 7 is a photocopy of a drawing of the lumbar vertebrae showing the posterior view. If the surgeon requires an access provided by the dilator retractor to be say, 35 mm, which is approximately 16 mm larger than the current available dilator retractors, the cylindrically shaped dilator retractor would have to be sized with a 35 mm diameter, as depicted by the circle X. Obviously, this sized dilator retractor would not fit into the contour of the vertebral body (spinous process) as it would be too wide in the horizontal direction, although sufficiently wide in the vertical direction. In accordance with this invention the major access of the elliptically shaped dilator retractor illustrated by the oval Z is in this example 35 mm and meets the requirement of the surgeon and the minor axis or narrower portion fits into the channel defined by the bone structure of this portion of the spine. In other words, the dilator retractor is contoured to the anatomical configuration of the patient or in other words is "tailored". It being noted that the 16 mm cylindrical dilator retractor, although narrow enough in the horizontal direction, is not sufficient in the vertical direction.

Figure 8:
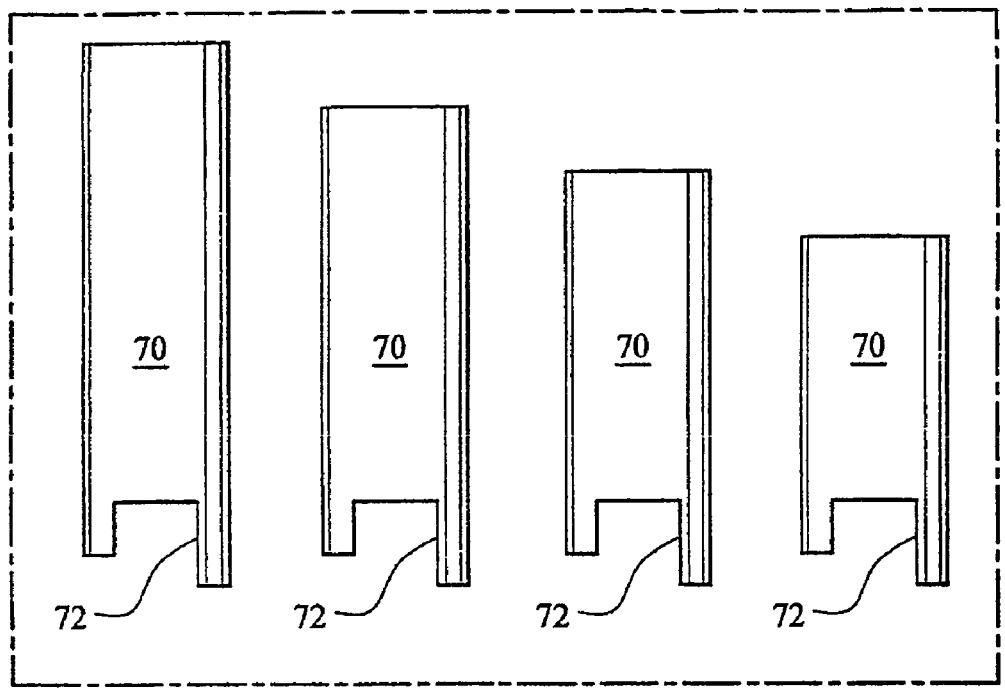
FIG. 8 is a schematic illustration of a series of different sized dilator retractors sized to accommodate different lengths to fit the anatomical dimensions of patients.
Figure 9:
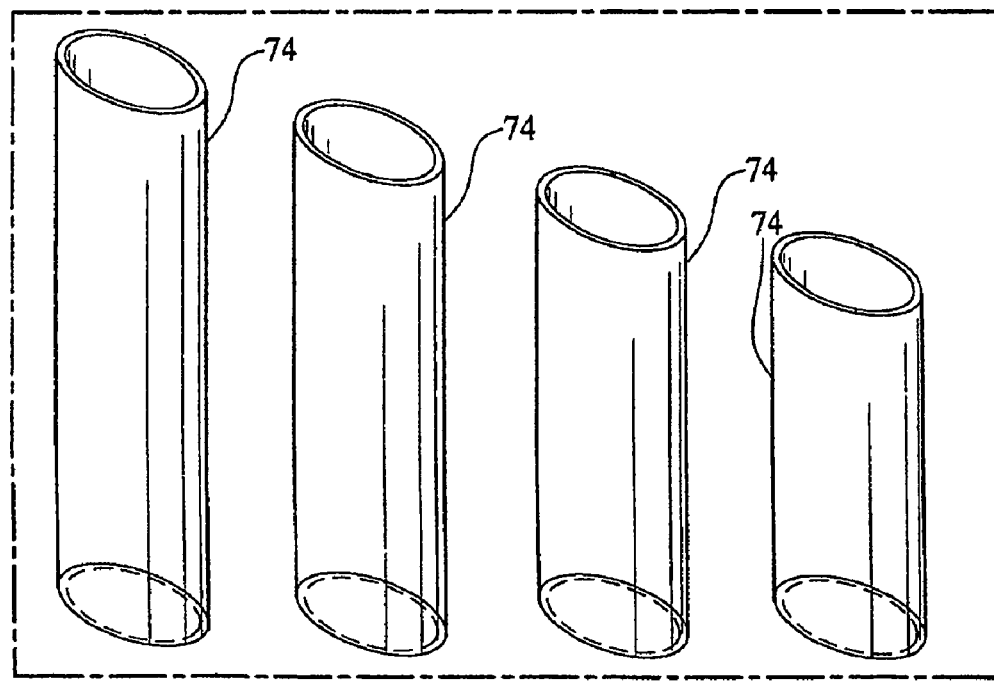
FIG. 9 exemplifies another series of varying length dilator retractors as would available to the surgeon.

FIGS. 8 and 9 exemplify embodiments of this invention where the particular "tailored" shape of the dilator retractor is provided in kits of different lengths to match the depth of the cavity of the working area of the patient. The kit may contain any number of sizes or alternatively, a facility, like a hospital, may inventory a given number of sizes and shapes of the dilator retractor. In the embodiment depicted in FIG. 8 a series of different length dilator retractors or cannulas 70 with the tunnel shaped distal end portion 72 are disclosed as a preferred embodiment and in FIG. 9 a series of different length ovoid dilator retractors 74 are depicted.

What has been shown by this invention is a novel, unique and functional dilator retractor that is "tailored" to meet the anatomical configuration of the patient. In addition, each of the configured dilator retractors are sized so that they conform to the depth of the cavity in which they are inserted into the patient. In addition to the benefits of these configured dilator retractors that have been enumerated above, these dilator retractors and the dilators associated therewith, afford opportunities to the surgeon to operate in areas of the spine that were not operable with minimal invasive surgery heretofore or at best were operable with a given risk.

Although this invention has been shown and described with respect to detailed embodiments thereof, it will be appreciated and understood by those skilled in the art that various changes in form and detail thereof may be made without departing from the spirit and scope of the claimed invention.

The invention claimed is:

1. A method of creating a working channel from a skin incision to proximate a vertebra, comprising:
   making a skin incision;
   inserting a distal end of a dilator into the skin incision;
   advancing the distal end of the dilator into proximity to a vertebra, the dilator extending from proximate the vertebra to external to the skin incision;
   inserting a cannula over the dilator, the cannula having a cut-out formed in a sidewall of the cannula at a distal end of the cannula;
   removing the dilator, a bore of the cannula defining a working channel from the skin incision to proximate the vertebra; and
   introducing an implant into a proximal end of the cannula and passing the implant through the cut-out in the sidewall of the cannula.

2. The method of claim 1, wherein the implant comprises a spinal rod.

3. A method of positioning an implant relative to a bone anchor, the method comprising:
   positioning a cannula such that a distal end of the cannula is in contact with a vertebra to define a working channel from a skin incision to a hone anchor coupled to the vertebra; and
   passing an implant through a cut-out formed in a sidewall of the cannula at a distal end of the cannula to position the implant relative to the bone anchor.

4. The method of claim 3, wherein the implant is a rod.

5. The method of claim 3, wherein the bone anchor is a pedicle screw.

6. A method of creating a working channel from a skin incision to proximate a vertebra, comprising:
   making a skin incision;
   inserting a non-cannulated dilator through the skin incision to position a distal end of the non-cannulated dilator in contact with a vertebra;
   inserting a plurality of cannulated dilators over the non-cannulated dilator to dilate the skin incision;
   inserting a cannula over the plurality of cannulated dilators to position a distal end of the cannula in contact with the vertebra, the cannula having a cut-out formed in a sidewall thereof; and
   removing the non-cannulated dilator and the plurality of cannulated dilators such that the cannula defines a working channel from the skin incision to proximate the vertebra;
   wherein, when the distal end of the cannula is positioned in contact with the vertebra, the cut-out formed in the sidewall of the cannula provides a lateral passage through the sidewall of the cannula for passing implants therethrough.

7. The method of claim 6, wherein the distal end of the cannula includes diametrically opposed lateral cut-outs formed in the sidewall thereof that provide diametrically opposed lateral passages.

8. The method of claim 6, further comprising passing an implant through the cut-out in the sidewall.

* * * * *